(12) United States Patent
Liu et al.

(10) Patent No.: US 11,092,581 B2
(45) Date of Patent: Aug. 17, 2021

(54) METHOD FOR ISOLATION AND RESTORATION FOR A MULTI CORE SENSOR SYSTEM WITHIN A TAXI

(71) Applicant: NOVA FITNESS CO., LTD., Shandong (CN)

(72) Inventors: Yiping Liu, Jinan (CN); Shuaishuai Jia, Jinan (CN); Lin Cheng, Jinan (CN); Shuchun Si, Jinan (CN); Michael Jun Xu, Lyons (FR)

(73) Assignee: NOVA FITNESS CO., LTD., Jinan (CN)

( * ) Notice: Subject to any disclaimer, the term of this patent is extended or adjusted under 35 U.S.C. 154(b) by 0 days.

(21) Appl. No.: 16/944,491

(22) Filed: Jul. 31, 2020

(65) Prior Publication Data
US 2020/0363385 A1 Nov. 19, 2020

Related U.S. Application Data

(63) Continuation of application No. PCT/CN2019/074037, filed on Jan. 31, 2019.

(30) Foreign Application Priority Data

Feb. 1, 2018 (CN) .......................... 201810102149.9
Jul. 25, 2018 (WO) .................. PCT/IB2018/055531

(51) Int. Cl.
*G01N 33/00* (2006.01)
*G01N 15/06* (2006.01)
(Continued)

(52) U.S. Cl.
CPC ......... *G01N 33/0006* (2013.01); *G01D 21/02* (2013.01); *G01N 15/0205* (2013.01); *G01N 15/0211* (2013.01); *G01N 15/06* (2013.01); *G01N 15/1012* (2013.01); *G01N 33/007* (2013.01); *G01N 33/0032* (2013.01);
(Continued)

(58) Field of Classification Search
CPC ........... G01N 33/0006; G01N 33/0032; G01N 33/0016; G01N 33/007; G01N 2015/0693; G01N 15/06
See application file for complete search history.

(56) References Cited

U.S. PATENT DOCUMENTS

2010/0274444 A1* 10/2010 Williamson ........... B64D 39/00
701/29.8
2013/0013241 A1 1/2013 Sill et al.

FOREIGN PATENT DOCUMENTS

CN 101763053 A 6/2010
CN 102480783 A 5/2012
(Continued)

*Primary Examiner* — Paul M. West

(57) ABSTRACT

A method for isolation and restoration for a multi-core sensor system within a taxi is provided. This method can intelligently determine whether the reason for an abrupt dramatic change in the data detected by sub-sensor is a sensor fault or sudden pollution, so as to increase the reliability of the data detected by the sub-sensor. This method can automatically determine if the repair can be performed when a device fault occurs, so as to ensure the continuity of the detection data of the sub-sensor, which has significant value for continuous monitoring required for a haze treatment operation. In addition, human and material resources for device maintenance may be saved, thereby reducing waste.

9 Claims, 10 Drawing Sheets

(51) Int. Cl.
*G01D 21/02* (2006.01)
*G01N 15/10* (2006.01)
*G01N 15/00* (2006.01)
*G01N 15/02* (2006.01)

(52) U.S. Cl.
CPC ............... *G01N 2015/0046* (2013.01); *G01N 2015/0693* (2013.01)

(56) References Cited

FOREIGN PATENT DOCUMENTS

| | | |
|---|---|---|
| CN | 105823856 A | 8/2016 |
| CN | 106066184 A | 11/2016 |
| CN | 106168520 A | 11/2016 |
| CN | 205691648 U | 11/2016 |
| CN | 107340014 A | 11/2017 |
| WO | 2017159514 A1 | 9/2017 |

\* cited by examiner

METHOD FOR ISOLATION AND RESTORATION FOR A MULTI CORE SENSOR SYSTEM WITHIN A TAXI

CROSS-REFERENCE TO RELATED APPLICATIONS

This application is a continuation of International Application No. PCT/CN2019/074037, filed on Jan. 31, 2019, which claims the benefit of priority from International Application No. PCT/IB2018/055531, filed on Jul. 25, 2018, and Chinese Patent Application No. 201810102149.9, filed on Feb. 1, 2018. The content of the aforementioned applications, including any intervening amendments thereto, is incorporated herein by reference.

TECHNICAL FIELD

This application relates to environmental monitoring, and particularly to a method for isolation and restoration for a multi-core sensor system within a taxi.

BACKGROUND OF THE DISCLOSURE

The monitoring indicators of atmospheric pollutants in environmental monitoring include sulfur dioxide, nitrogen oxides, ozone, carbon monoxide, $PM_1$ (particles with aerodynamic particle size less than 1 μm), $PM_{2.5}$ (particles with aerodynamic particle size less than 2.5 μm), $PM_{10}$ (particles with aerodynamic particle size less than 10 μm), $PM_{100}$ (particles with aerodynamic particle size less than 100 μm), and VOCs (volatile organic compounds) or TVOC (total volatile organic compounds). The atmospheric environment monitoring system can collect and process the monitoring data, and reflect the air quality condition and change law of the regional environment in a timely and accurate manner.

At present, the atmospheric environment monitoring equipment mainly includes fixed monitoring stations and mobile monitoring equipment. The current fixed monitoring stations are mainly divided into large fixed monitoring stations and small monitoring stations. Mobile monitoring equipment mainly includes special atmospheric environmental monitoring vehicles, drones and handheld devices. The aforementioned small monitoring stations and handheld devices all use air quality sensors to measure pollutants in the atmosphere. Air quality sensors have the characteristics of low cost, miniaturization and online monitoring, and can be used on a large scale. However, the air quality sensor itself has errors due to various reasons that cause the measured value to be inconsistent with the true value, and it also has low accuracy, poor stability, large errors, and requires frequent calibration compared with large precision instruments or manual monitoring methods.

The laser scattering method for air pollution particulate matter sensors has a broad market prospect because of its low cost and portability. In the prior art, the portable analysis device of the air particulate matter sensor using the laser scattering method has disadvantages such as poor measurement consistency, large noise, and low measurement accuracy. The core device is susceptible to various environmental factors, and the fluctuations of the core device easily cause misjudgment.

When the sensor data changes suddenly and sharply, being able to intelligently determine whether the change is due to sensor failure or sudden pollution will greatly improve the reliability of the data and is of great value for ensuring the quality of monitoring data. When the equipment fails, if it can be repaired automatically, the online rate of the data can also be greatly improved, which is of great value for the continuous monitoring required for haze control. At the same time, it can save manpower and material resources in equipment maintenance and reduce social waste.

Chinese Patent Application Publication No. 105823856 A discloses an air quality monitoring method based on multi-sensor fusion, which fuses multiple sets of measurement data from multiple sensors to optimize the problem of pseudo-random errors introduced by the fluctuation of light. The data fusion method can select the existing fusion algorithm according to the requirements.

The article discloses that when the scattering method is used to measure pollutants in the air, the emitted laser is in the range of several hundred nanometers to more than one thousand nanometers, And for $PM_{2.5}$ (particle diameter below 2500 nm) and $PM_{10}$ (particle diameter below 10000 nm) pollutants to be tested, the visible laser wavelength is equivalent to the particle size of the pollutant to be measured. The laser light shows both fluctuation and particle at the same wavelength, and the scattering effect used by the light scattering method can only be measured by the particle of light, so the one time measurement cannot fully accurately represent the number of particles in the space to be measured.

Chinese Patent Application Publication No. 101763053 A discloses a detection system with a real-time self-diagnostic function, capable of identifying sensor failure, signal abnormality, subsystem function failure, or system abnormality. When the sensor fails, the system can immediately upload the fault information and activate the alarm; at the same time, isolate the fault sensor.

Chinese Patent Application Publication No. 102480783 A discloses a wireless sensor system, which can make redundant nodes in the network rotational rest irregularly through the watch keeping scheduling mechanism to extend the life.

SUMMARY OF THE DISCLOSURE

Terminology

Sensor: A sensor is a detection device that can sense the concentration information of pollutants and can convert the sensed information into electrical signals or other required forms of information output in accordance with a certain rule to meet the transmission, processing, storage, display, record, and control requirements. The pollutants in this article mainly include particulate matter ($PM_1$, $PM_{2.5}$, $PM_{10}$, $PM_{100}$), nitrogen oxides, sulfur dioxide, ozone, VOCs/TVOC and carbon monoxide.

Sub-sensor: It is also called sub-sensor unit. In this article, the sub-sensor includes fan, sensing element, MCU, signal conversion element and signal amplification circuit. It can independently complete the collection and calculation of pollutant data and can also transmit to local for data storage.

Sensor module: The sensor module is a sensor device composed of multiple sub-sensors. The sub-sensors are also called cores in the sensor module. For example, a sensor module consisting of four sub-sensors is called a quad-core sensor, and a sensor module consisting of five sub-sensors is also called a five-core sensor.

Abnormal fluctuation of sub-sensor: indicates that the discrete degree of the measurement results of the sub-sensor during continuous measurement exceeds the normal range.

Abnormal drift of sub-sensor: It means that the average value of the measurement result of the sub-sensor during continuous measurement is shifted from the true value beyond the normal range.

Abnormal correlation of sub-sensor: indicates that the correlation between the measurement results of the sub-sensor during the continuous measurement and other sub-sensors is lower than the normal range.

Abnormal of sub-sensor: Abnormal fluctuation of sub-sensor, abnormal drift of sub-sensor, and abnormal correlation of sub-sensor are all abnormal of sub-sensor.

Abnormal sub-sensor: Also called a fault sub-sensor, it is a sub-sensor in which the abnormal phenomenon of the sub-sensor occurs.

The suspected abnormal sub-sensor: Also called suspected faulty sub-sensor, in the sensor module, the sub-sensor with the largest fluctuation or drift does not trigger the isolation condition; that is, the degree of fluctuation or offset cannot make it be regarded as an abnormality of the sub-sensor. The suspected abnormal sub-sensor is the closest abnormal of sub-sensor among the normal sub-sensors. For example, if the measured value deviates from the normal value by 20%, it is judged to be abnormal. Assuming that the number 1, 2 and 3 sub-sensors deviate from the normal values by 5% and 6%, 16%, and then we judge the sub-sensor 3 is a suspected abnormal sub-sensor.

Isolation: The case where the sub-sensor does not participate in the operation of the value uploaded by the control module is called sub-sensor isolation.

Isolation condition: The isolation condition is used to determine whether the suspected abnormal sub-sensor needs to be isolated. Such as the value of the degree of dispersion in the abnormal fluctuation of sub-sensor, and the offset value of the abnormal drift of sub-sensor.

Recovery condition: The recovery condition is the basis for judging whether the sub-sensors in the isolation zone will resume work. The standard of the recovery condition should be appropriately higher than the isolation condition, and there should be a difference of at least 10% from each other to avoid the newly recovered sub-sensors from being isolated again.

Rotational rest method: It is a kind of working method of sub-sensors, which means that the sub-sensors start and stop work alternately at intervals.

Data deterioration: indicates that the range of sub-sensor value deviates from the normal value increases.

Due to various reasons, for example, the performance of the sub-sensor itself and the influence of external interference, there is often a small error between the measured value and the true value of the air quality sensor. Reducing errors and improving accuracy are the efforts in the field of sensors.

There are also many ways to improve sensor accuracy.

The first method is to use a single high-cost and high-precision sensor, but the problems brought by it are also obvious. In addition to the high cost problem, it is not possible to determine whether the sensor is abnormal through the data output by the sensor itself.

The second method is a dual-core sensor, which independently measures and outputs the results through two sub-sensors. This method can compare the output results of the two sub-sensors according to a certain judgment standard to determine whether the sub-sensor works abnormally, but this method cannot determine which sub-sensor has an abnormality.

The third method is a triple-core sensor. By comparing the output results of the three sub-sensors, it is determined which sub-sensor has a problem, and then isolates the sub-sensor. However, since the sensor module runs in dual-core mode after isolating a sub-sensor, there will be a problem that the abnormal sensor cannot be judged. Therefore, once one sub-sensor of the three-core sensor is abnormal, the reliability of the whole sensor module is greatly reduced.

FIG. 1 shows the working state of the sub-sensor. The sub-sensor 100 indicates a normal sub-sensor. The sub-sensor 101 and the sub-sensor 102 are suspected abnormal sub-sensors. The sub-sensor 104 indicates an abnormal sub-sensor. In FIG. 2, 1U indicates a one-core sensor mode. When the sub-sensor data is abnormal, it cannot be determined whether the sensor itself is faulty or the air quality is abnormal. 2U indicates a dual-core sensor module. When the dual-core sensor module has a sub-sensor output abnormal, it cannot determine which one is abnormal, so one sub-sensor of the dual-core sensor module is abnormal, and the entire module cannot work normally. By analogy, 3U represents a three-core sensor module.

In view of the above-mentioned shortcomings, the present disclosure provides a method for isolation and restoration for a multi-core sensor system within a taxi. The disclosure uses a sensor module consisting of at least four sub-sensor, which realizes complementary data deviations and mutual verification, and improves the reliability, consistency, accuracy and life of the sensor module.

As shown in FIGS. 3 and 4, 4U represents a quad-core sensor module. When a sub-sensor is detected to have a suspected abnormality, and the suspected abnormal sub-sensor further shows sub-sensor abnormality, the sub-sensor is determined as an abnormal sensor and isolated. The quad-core sensor module downgraded to a three-core sensor module, the three-core sensor module can still work normally. 5U means a five-core sensor module. When a sub-sensor is detected to have a suspected abnormality, and the suspected abnormal sub-sensor further shows sub-sensor abnormality, the sub-sensor is determined as an abnormal sensor and isolated. The five-core sensor module is downgraded to a quad-core sensor module, and the quad-core sensor module can still work normally; and so on, the six-core sensor module, the seven-core sensor module and more core sensor modules.

The multi-core sensor system is installed in the ceiling light of the taxi; the multi-core sensor system includes a gas separation box, a control module and a detection module. The gas separation box is used to distribute the measured gas to each individual sub-sensor. The gas inlet of the gas separation box is connected to the gas sampling head, and the gas outlet is connected to the air inlet of each sub-sensor of the detection module. The detection module is a sensor module with four or more sub-sensors built in and it is used to detect the concentration of atmospheric pollutants. The control module is used to receive, analyze and upload the data detected by the detection module, and supply power to the detection module.

The sub-sensor types include $PM_1$ sensor, $PM_{2.5}$ sensor, $PM_{10}$ sensor, $PM_{100}$ sensor, sulfur dioxide sensor, nitrogen oxide sensor, ozone sensor, carbon monoxide sensor, VOCs sensor, TVOC sensor and other sensors that can measure the concentration of environmental pollutants.

The detection accuracy of the sub-sensor is related to many factors, such as the measured gas flow rate and temperature. The disclosure further improves the detection accuracy of the sensor module by designing in various ways.

The detection accuracy of the sub-sensor is related to temperature. As shown in FIG. 8, the sub-sensor has an optimal operating temperature range. When the temperature is higher than the optimal operating temperature, the detection accuracy will decrease. In the disclosure, the temperature of the sensor and the intake air are adjusted by a temperature control device, and can be compensated by an algorithm to improve the detection accuracy.

The detection accuracy of the sub-sensor is also related to the flow rate of the measured gas flowing inside the sub-sensor. As shown in FIG. 9, the measured gas has the highest accuracy at the optimal flow rate $V_0$. Too fast or too slow the measured gas flow rate will affect the detection accuracy of the sub-sensor. The internal air resistance of the sub-sensor or other reasons will cause the measured gas flow rate to change, as shown in FIG. 10. The present disclosure controls the measured gas flow rate within the optimal flow rate range by adjusting the internal fan speed or other flow rate adjustment methods to improve the detection accuracy of the sub-sensor.

Multi-core sensor modules use embedded algorithms to solve the problem of out-of-synchronization of multiple sub-sensors in detecting sampling gas due to different lengths of intake pipes, thereby obtaining more accurate detection data.

Multi-core sensor modules use multiple sub-sensors to measure air quality at the same time, and the output value is the average value of multiple sub-sensors, with high data accuracy. FIG. 5 shows the output data of the quad-core sensor module, where U1, U2, U3, and U4 are the output data of the four sub-sensors, and the solid line Average is the average of the four sub-sensors, so the output data is smoother, Stability and higher accuracy.

Laser sensor performance is affected by light decay of laser. As the semiconductor laser is used for a longer time, the problem of optical power attenuation due to semiconductor materials and production processes will occur. When the optical power attenuation reaches a certain level, the accuracy of the laser sensor detection data will be affected.

In order to understand the variation degree of light attenuation of a group of laser sensors after working for a long time, the disclosure divides the sensor group into a high frequency group and a low frequency group, in which the low frequency group serves as a redundant unit to provide a calibration basis for the high frequency group.

The disclosure discloses another multi-core sensor system, which is installed in a ceiling lamp of a taxi; the multi-core sensor system includes a control module and a detection module. The detection module comprises a sensor module consisting of at least two similar sub-sensors and the sub-sensor operates at a normal operating frequency. The detection module also includes a low-frequency calibration module consisting of at least one sub-sensor, and the sub-sensor in low-frequency calibration module is similar to the sub-sensor in the sensor module; the sub-sensor in the low-frequency calibration module operates at a frequency lower than the operating frequency of the sensor module. Therefore, the low-frequency calibration module is also called a low-frequency group. For comparison, the sensor module is also called a high-frequency group.

Generally, the operating frequency of the sensor module is 10 times or more than that of the low-frequency calibration module. The sensor module and the sub-sensors of the sensor module have the same operating frequency, and the low-frequency calibration module and the sub-sensors of the low-frequency calibration module have the same operating frequency. The ratio of the operating frequency of the sensor module to the operating frequency of the low-frequency calibration module is called the high frequency and low frequency ratio, and can be set as: 2:1, 3:1, 4:1, 5:1, 6:1, 7:1, 8:1, 9:1, 10:1, 15:1, or 20:1.

The operating frequency of the low-frequency calibration module can be consistent with the rhythm of abnormal judgment. That is, when it is necessary to determine whether there is the phenomenon of an abnormal sub-sensor in the sensor module, the low-frequency calibration module performs the detection work.

Because the laser power attenuation is slow in most of the working life of the laser sensor, the accuracy of its data can be restored by calibration; that is, the sub-sensor that is not attenuated or has a very low attenuation is used to calibrate the high-attenuated sub-sensor.

During the operation of the sensor module, every certain time, such as 1 day, 1 week, or 1 month, use the detection data of the low-frequency calibration module as a reference to calibrate the detection data of the sensor module, and the calibration coefficient can be obtained by the ratio of the average value of the detection data of the sensor module to the average value of the detection data of the low-frequency calibration module.

In addition to the light attenuation effect of laser sensors, other types of sensors may also have a tendency of unstable performance or increased data errors under long-term high-load working conditions. By introducing a low-frequency calibration module, it can be used as a relatively reliable reference to determine whether there is a data shift phenomenon in the sensor module.

At the same time, since the data of the low-frequency calibration module is generally more reliable, when determining which sub-sensor in the sensor module is suspected to be abnormal or abnormal, a more reliable judgment can be made by increasing the data weight of the low-frequency calibration module. A simple solution is that all the data from the low-frequency calibration module is involved in the judgment of suspected anomalies with twice the weight.

The low-frequency calibration module can also participate in the judgment of suspected anomalies by adopting the following schemes to distinguish situations:

1) Single low frequency sensor: the data weight of the low frequency sensor is 2; the data weight of each sub-sensor in the sensor module is 1;

2) Two low-frequency sensors: Based on the average value of the sensor module, the data weight of one low-frequency sensor closer to the reference value is 2, and the weight of the other low-frequency calibration module is 1.

3) Three or more low-frequency sensors: Based on the average value of the data in the low-frequency calibration module, the ones that deviate farthest from the reference in the sensor module are suspected anomalies.

When the control module detects a suspected abnormality in one of the sub-sensors in the sensor module, and the suspected abnormal sub-sensor further shows sub-sensor abnormality, the sub-sensor is determined as an abnormal sensor, it is isolated and classified into an isolation area, and the multi-core sensor module continues to work normally after it is degraded.

The disclosure also discloses a method for isolation and restoration for a multi-core sensor system within a taxi. The method is shown in FIG. 11. The sensor module obtains a set of detection data at a time, and the control module filters out suspected abnormal data from this set of data, and then determines whether the corresponding sub-sensor meets the isolation condition. The sub-sensor was judged to be abnormal sub-sensor and then classified into the isolation zone; after judging that the suspected abnormal sub-sensor does not meet the isolation condition, the sub-sensor continues to work normally. Determine whether the abnormal sub-sensor entering the isolation area can heal itself. If it can heal itself, the frequency reduction will be performed. However, the output data of the abnormal sub-sensor will not participate in the calculation of the output data of the main control module. For abnormal sub-sensors that cannot self-heal, stop working and notify the operator to repair or replace them. For the abnormal sub-sensor after frequency reduction, the control module detects its output data to judge whether it meets the recovery condition. If the abnormal sub-sensor can meet recovery condition, the abnormal sub-sensor that meets the recovery condition is removed from the isolation zone, and the abnormal sub-sensor will be determined as the initial sub-sensor and resume to work. The output data is involved in the calculation of sensor module data or master control data. For the abnormal sub-sensor that does not meet the recovery condition, whether it can be self-healing is determined again.

After isolating the abnormal sub-sensors in the sensor module, the average value of the remaining sub-sensor output data is used as the output result of the sensor module, and the sensor module can continue to be used normally.

The present disclosure sets a rotational rest mode for the sensor module. Among the sub-sensors that work normally, one or more rotational rests are selected, which can solve the problem of reduced performance due to sub-sensor fatigue.

With the increase of working time, the internal state of the sub-sensor will change to a certain extent. For example, the internal temperature will increase with the increase of working time, and the mechanical components of the sampling device will suffer from metal fatigue. Therefore, an appropriate rest after working for a period of time will restore the sub-sensor to its optimal working state.

The sub-sensor enters the stable working period after starting for a period of time, but after a long period of continuous work, the fatigue will increase. In order to alleviate this situation, those sub-sensors that have entered a fatigue state can be selected to be put into a rest state to reduce the data offset of the sensor fatigue stage, and try to make the sub-sensor work in a stable working period.

For the laser sensor module, the rotational rest can also keep the light attenuation of the same group of sub-sensors basically synchronized.

With the use of semiconductor lasers for a long time, there will be a problem of attenuation of the light output power due to the decrease in the efficiency of semiconductor materials. When a semiconductor laser is used as a light emitting element, the light scattering emission particle sensor needs to consider the light attenuation synchronization between sub-sensors when it contains multiple sub-sensors.

If the light attenuation between the sub-sensors is not synchronized, when the light attenuation is light, its impact on the data is relatively small, although there will be some differences in the data of each sub-sensor, but it is impossible to determine whether the sub-sensor is faulty based on these lighter differences. But these data will still participate in the calculation of the final detection data of the sub-sensor and result in deviations in the final detection data.

Therefore, the control module of the multi-core sensor system should record and store the cumulative working time of each sub-sensor, adjust the rotational rest interval of each sub-sensor according to the cumulative working time, and keep the light attenuation of each sub-sensor basically synchronized, which is conducive to the improvement of sub-sensor detection data accuracy.

The disclosure has low use cost. Compared with expensive precision instruments, the sensor module only adds a few sub-sensors, which does not significantly increase the overall cost of the device. However, Due to the increase in reliability and accuracy, it is also possible to apply low-precision, low-reliability, low-cost sub-sensors to situations where only high-precision instruments can be used. The multi-core sensor module also extends the life and maintenance cycle of the entire monitoring equipment, reducing the cost of equipment replacement and repair.

Sub-sensor failure judgment can be done through the local master control module, or through the data center online monitoring system. The online monitoring system is responsible for receiving data, storing data, data processing, and generating visual pollution cloud maps.

Figure 1:
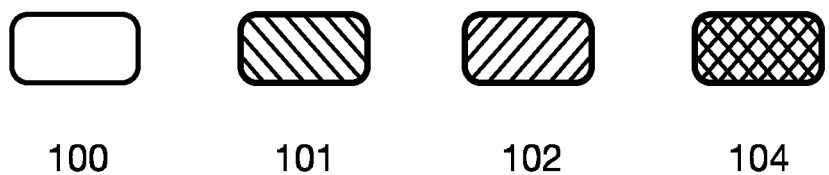
FIG. 1 is the schematic diagram of a state of a sub-sensor.
Figure 2:
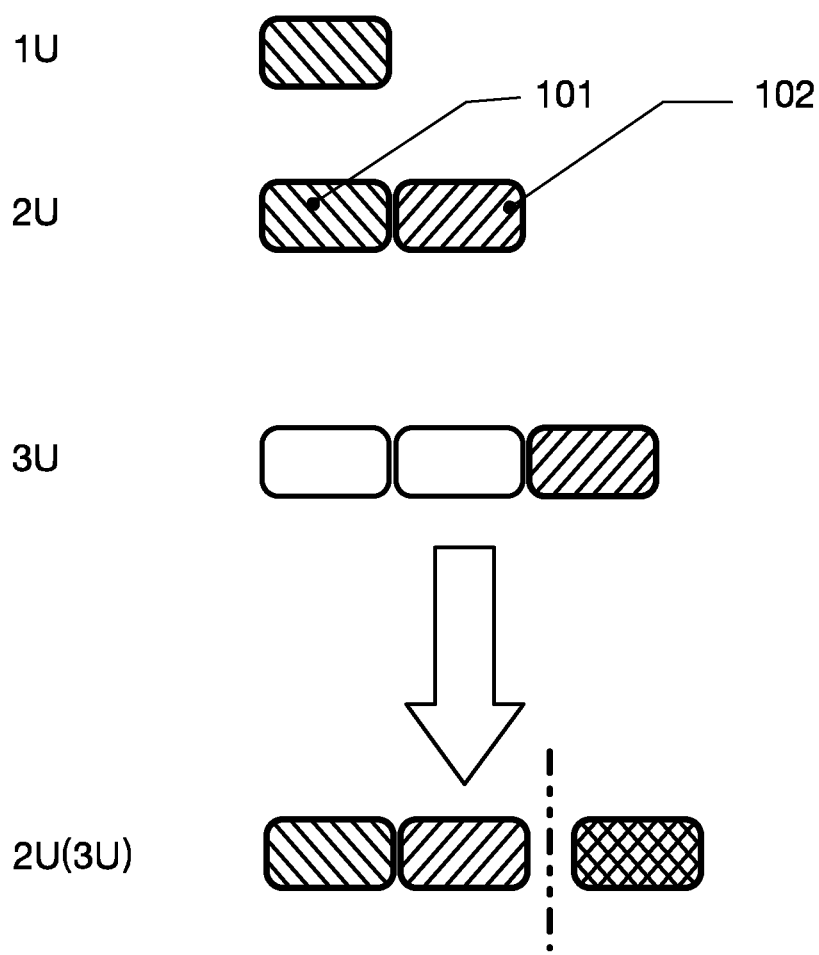
FIG. 2 is the schematic diagram of a single sensor failure of a single-core sensor module, a dual-core sensor module, a triple-core sensor module, and a triple-core sensor module.

In the drawings: 100—normal sensor, 101—suspected abnormal sub-sensor (one), 102—suspected abnormal sub-sensor (two), 104—abnormal sub-sensor, U3—sensor 3, U3—d-status indicator (Red-fault), U4—d-status indicator (green-normal); 2U (3U)—represents a group of three-core sensors operating in two-core mode, with one core isolated.

DETAILED DESCRIPTION OF EMBODIMENTS

The multi-core sensor system includes a gas separation box, a control module and a detection module. The gas separation box is used to distribute the measured gas to each individual sub-sensor. The gas inlet of the gas separation box is connected to the gas sampling head, and the gas outlet is connected to the air inlet of each sub-sensor of the detection module. The detection module is a sensor module with four or more sub-sensors built in and it is used to detect the concentration of atmospheric pollutants. The control module is used to receive, analyze and upload the data detected by the detection module, and supply power to the detection module. The gas separation box has a buffer function to relieve pressure fluctuations.

The detection module may also include a low-frequency calibration module consisting of at least one sub-sensor, and the sub-sensor in the low-frequency calibration module is similar to the sub-sensor in the sensor module; the operating frequency of the sub-sensor in the low-frequency calibration module is much lower than the sub-sensor in the sensor module. In a multi-core sensor system including a low-frequency calibration module can reduce to two or three sub-sensors.

The control module is provided with a control module data communication interface which is connected with the sub-sensor data communication interface by wires. The sub-sensor transmits data to the control module through the data communication interface of the control module connected to the sensor. The detection module is connected to the control module through a data interface. The control module can not only process the detection data of the sub-sensors, but also upload the data to the data center through the wireless network to implement the data uploading and positioning functions. The data center is responsible for receiving data, storing data and processing data. The online monitoring system can manually control the secondary calibration of the abnormal sensor.

Figure 3:
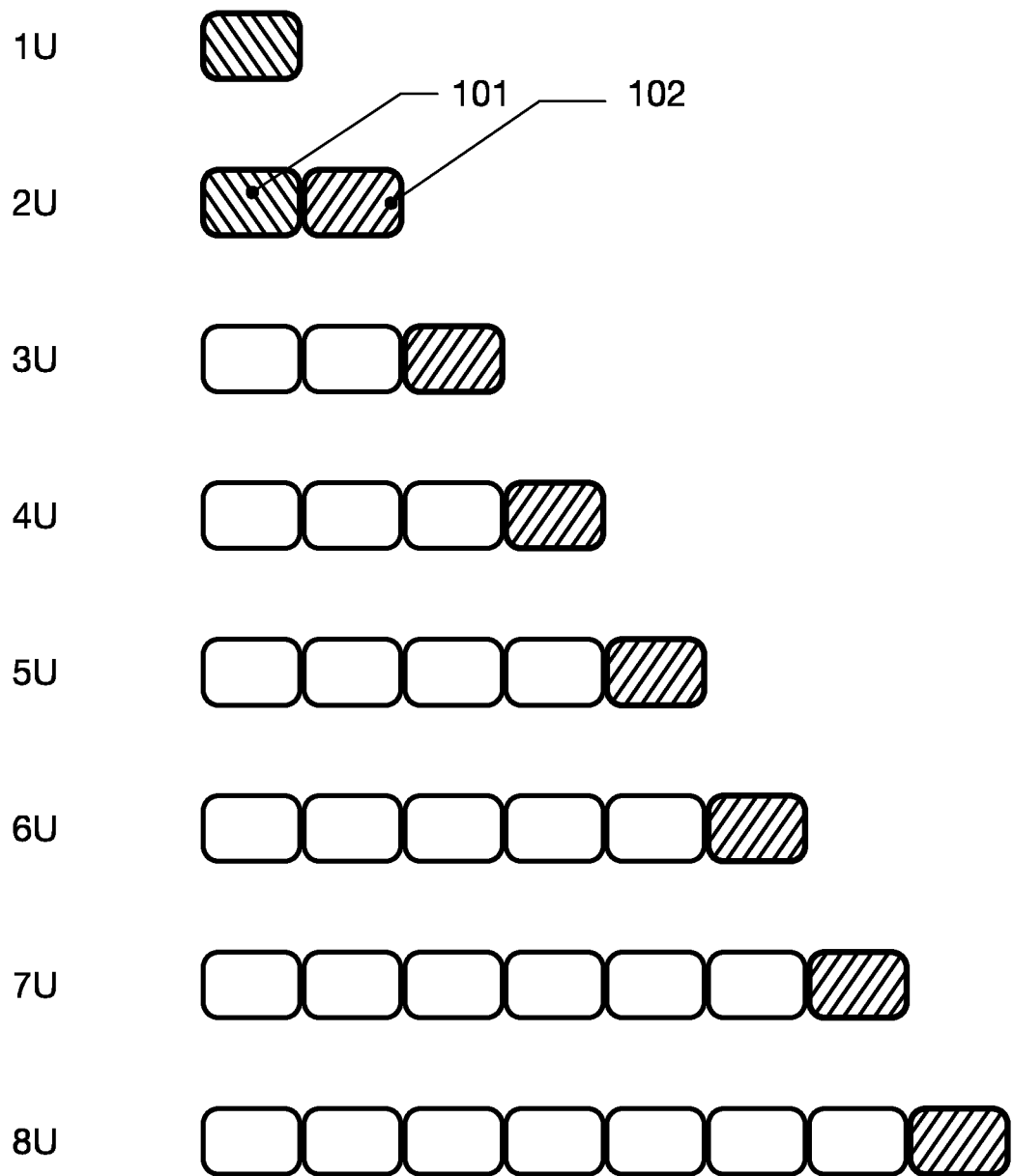
FIG. 3 is the schematic diagram of judging a suspected abnormal sub-sensor module. For one-core and dual-core sensor modules, abnormal conditions cannot be determined after suspected abnormalities; sensor modules with three or more cores can determine sensors suspected of abnormalities.
Figure 4:
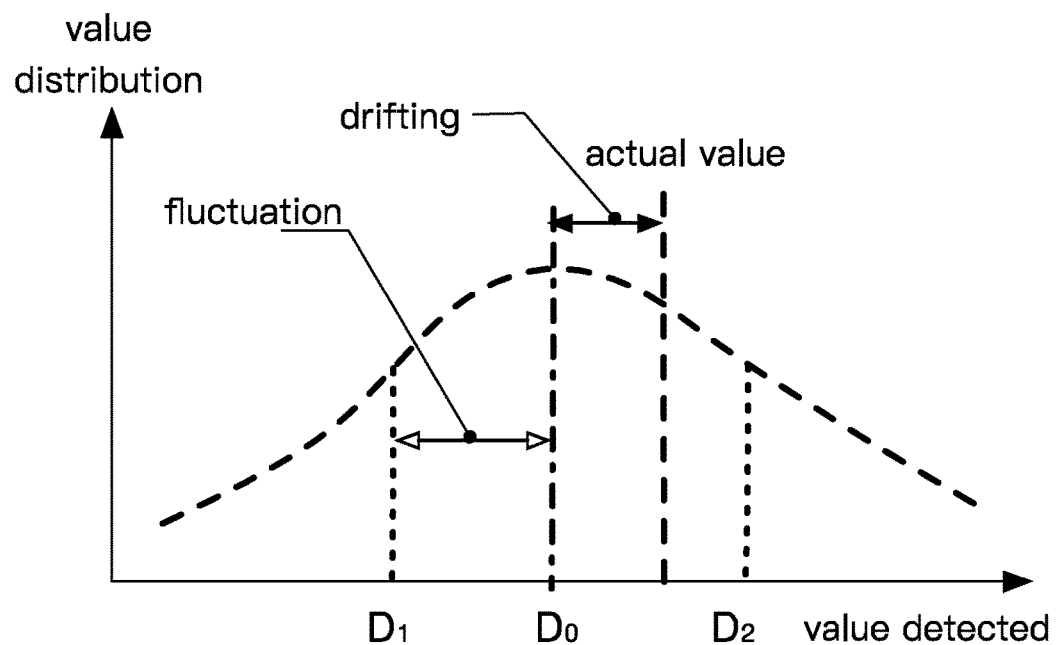
FIG. 4 is the sensor error diagram, Do and Di are fluctuations; Do and actual values are drifting.
Figure 5:
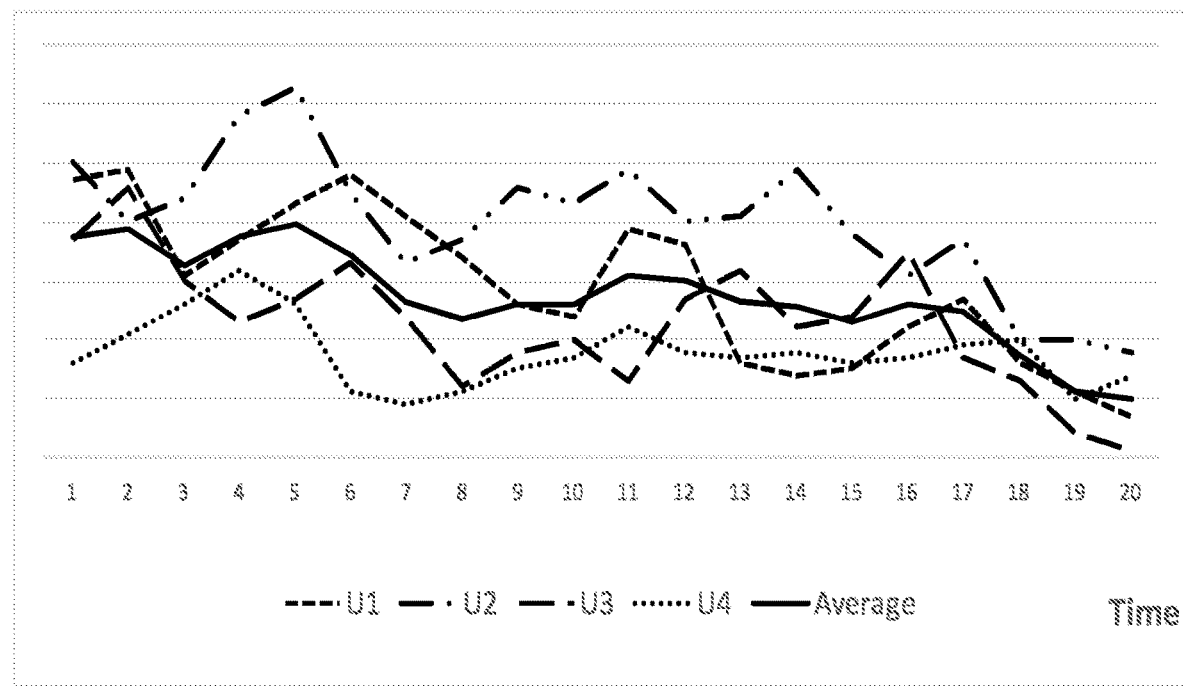
FIG. 5 is a schematic diagram of the output data of the quad-core sensor module and its sub-sensor output, Average is the quad-core average output result, and the dotted line is the output result of each core.
Figure 6:
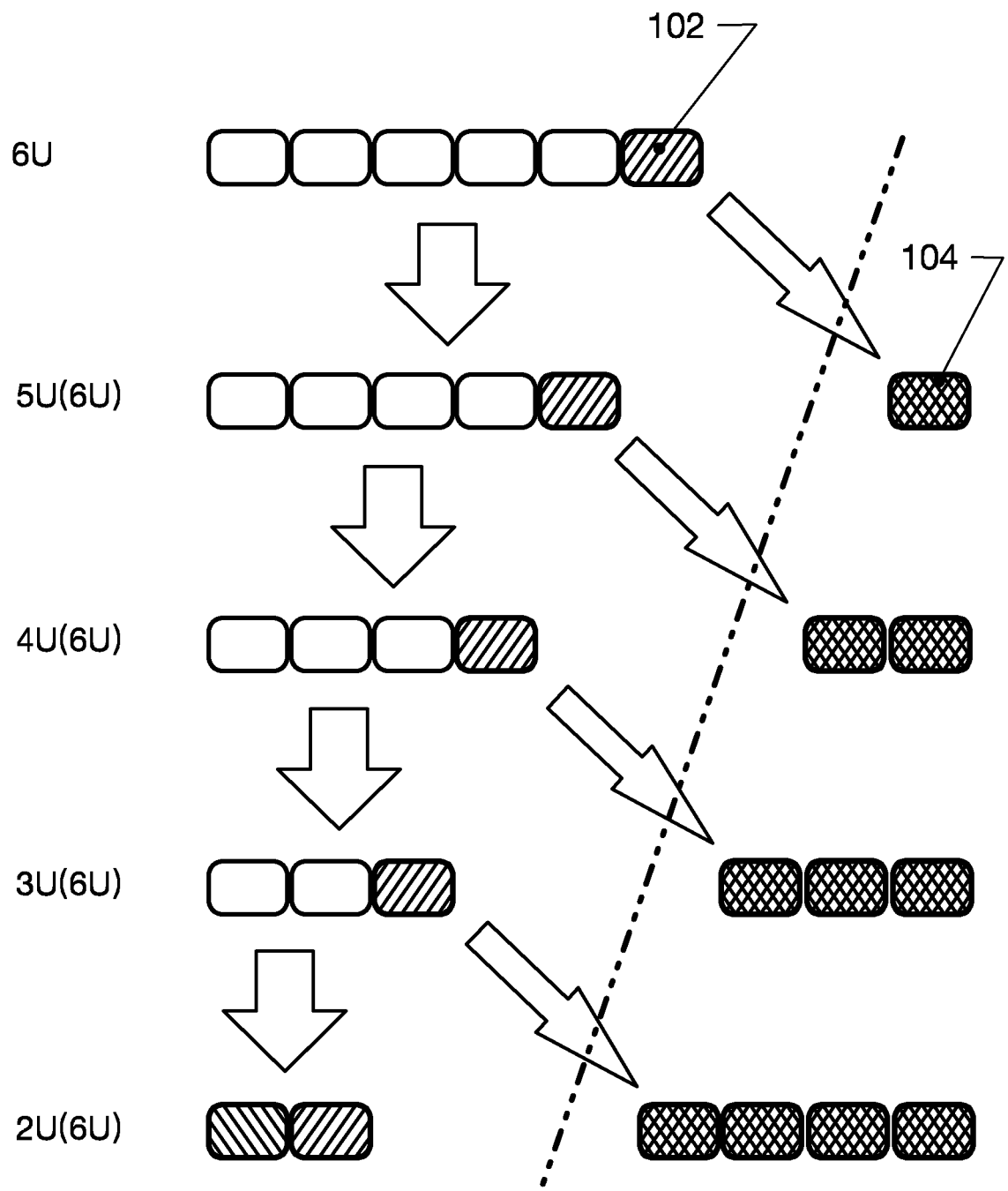
FIG. 6 is the schematic diagram of an isolation method for an abnormality of a sub-sensor of a six-core sensor module.
Figure 7:
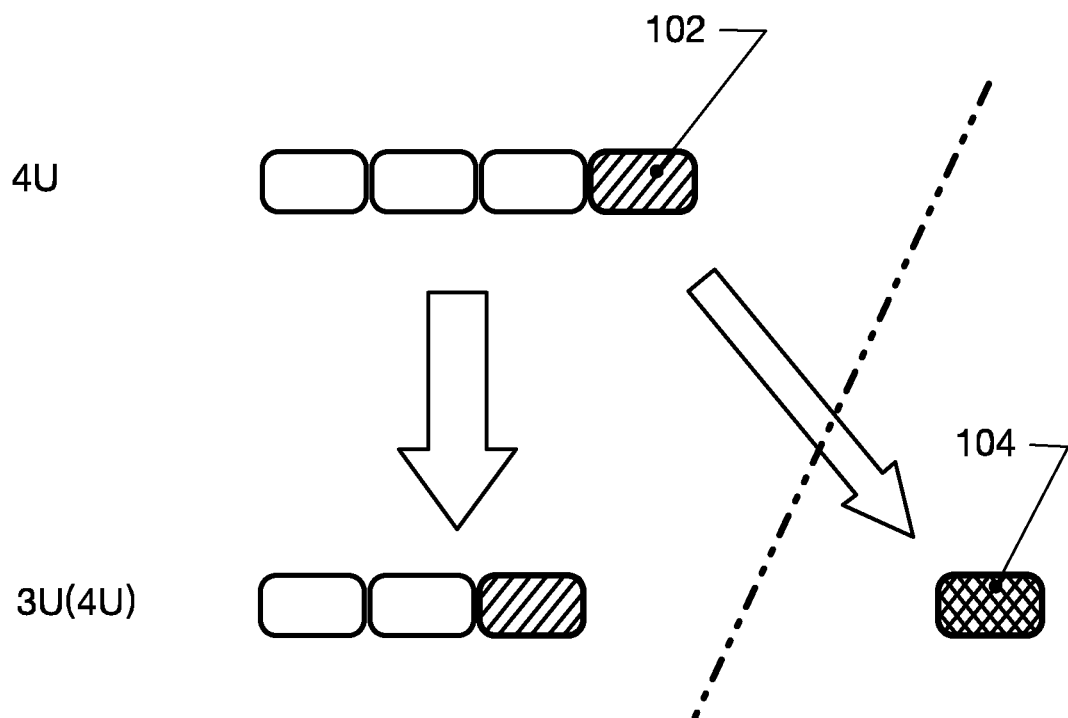
FIG. 7 is a schematic diagram of isolation and recovery an abnormal sensor in a quad-core sensor module.
Figure 7:
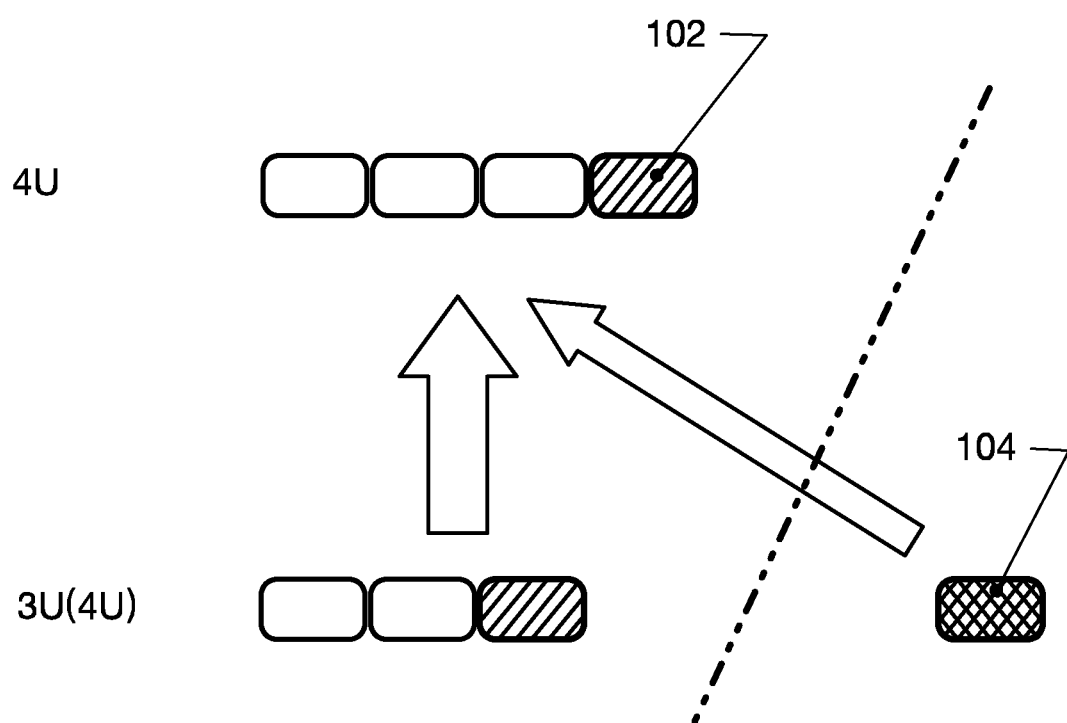

The disclosure adopts a sensor module consisting of multiple sub-sensors, which realizes complementary data deviations and mutual verification, and improves the reliability, consistency, accuracy and life of the sensor module. As shown in FIGS. 3 and 4, 4U represents a quad-core sensor module. When a sub-sensor is detected to have a suspected abnormality, and the suspected abnormal sub-sensor further shows sub-sensor abnormality, the sub-sensor is determined as an abnormal sensor and isolated. The quad-core sensor module downgraded to a three-core sensor module, the three-core sensor module can still work normally. 5U means a five-core sensor module. When a sub-sensor is detected to have a suspected abnormality, and the suspected abnormal sub-sensor further shows sub-sensor abnormality, the sub-sensor is determined as an abnormal sensor and isolated, the five-core sensor module is downgraded to a quad-core sensor module, and the quad-core sensor module can still work normally; and so on, the six-core sensor module, the seven-core sensor module and more core sensor modules.

Humidity and Temperature Adjustment

Figure 8:
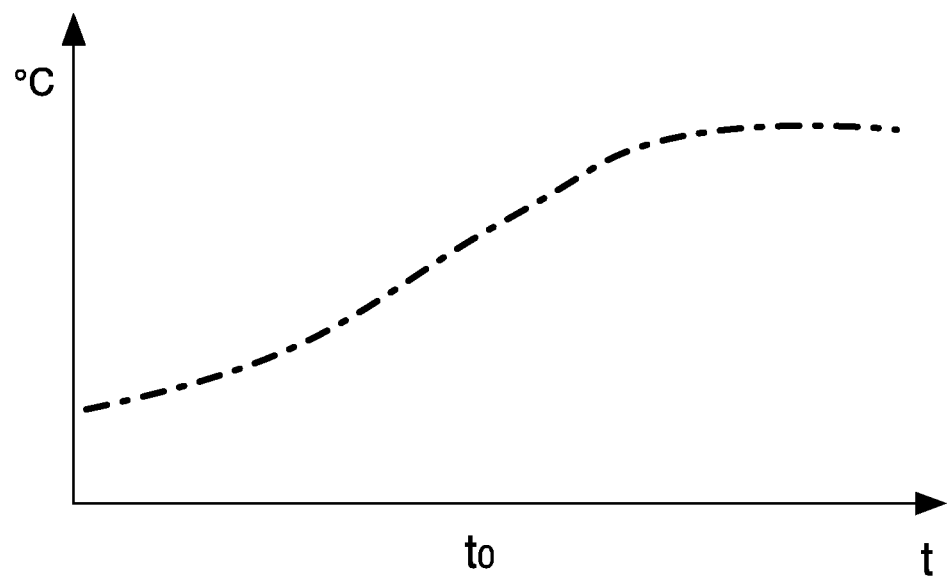
FIG. 8 is a schematic diagram of the relationship between the detection accuracy of the sensor and the temperature.
Figure 8:
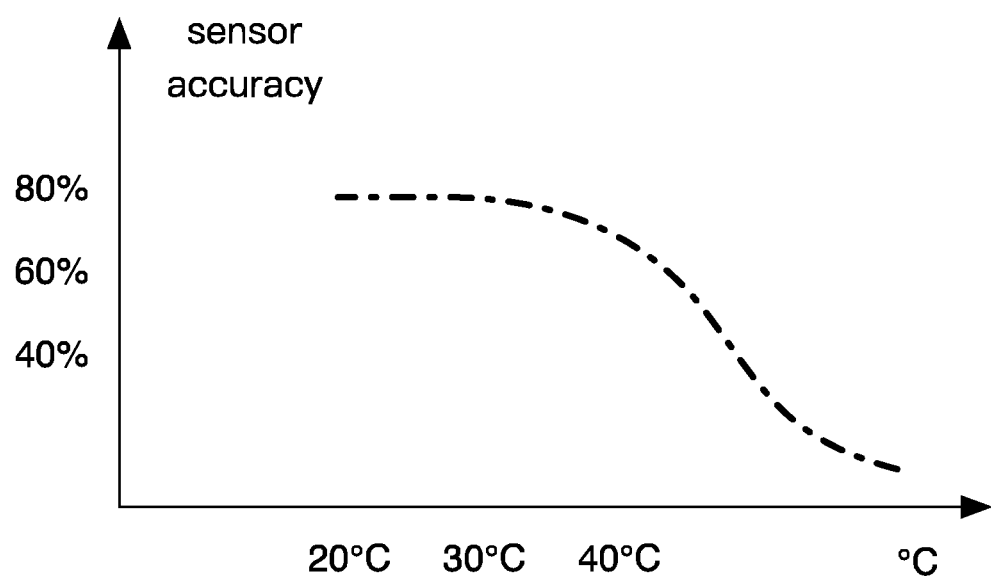

The detection accuracy of the sub-sensor is related to temperature. As shown in FIG. 8, the sensor has an optimal operating temperature range. When the temperature is higher than the optimal operating temperature, the detection accuracy will decrease. In the disclosure, the temperature of the sensor and the intake air are adjusted by a temperature control device.

Embodiment One

The gas separation box can be equipped with a semiconductor refrigerating sheet capable of heating and dehumidifying. The semiconductor refrigeration sheet is metal, and the semiconductor refrigeration sheet includes a hot end and a cold end. Use the hot end of the semiconductor refrigeration sheet to directly heat the gas separation box, and install a humidity sensor before the gas inlet of the gas separation box. The control module turns on the semiconductor refrigeration sheet when the humidity of the gas measured is greater than the set value upper limit (the upper limit of the set value can be 60%, 65%, 70%, etc.); when the gas humidity measured by the humidity sensor is less than the lower limit of the set value (the lower limit of the set value can be 40%, 50%, etc.), the control module makes the semiconductor refrigeration sheet stop heating and dehumidifying.

Embodiment Two

The gas separation box can be equipped with a semiconductor refrigerating sheet with heating and dehumidification functions. The semiconductor refrigeration sheet is metal, and the semiconductor refrigerating sheet includes a hot end and a cold end. The gas separation box is directly heated by the hot end of the semiconductor refrigerating sheet, and the cold end of the semiconductor refrigerating sheet is connected to the heat-dissipating grille, and the air-distributing box is cooled through the heat-dissipating grille. Install a humidity sensor before the air inlet of the gas separation box. The control module turns on the semiconductor refrigerating sheet when the humidity of the gas measured is greater than the set value upper limit (the upper limit of the set value can be 60%, 65%, 70%, etc.); when the gas humidity measured by the humidity sensor is less than the lower limit of the set value (the lower limit of the set value can be 40%, 50%, etc.), the control module makes the semiconductor refrigeration sheet stop heating and dehumidifying.

Embodiment Three

The gas separation box can be equipped with a semiconductor refrigerating sheet capable of heating and dehumidifying. The semiconductor refrigeration sheet is metal, and the semiconductor refrigeration sheet includes a hot end and a cold end. Use the hot end of the semiconductor refrigeration sheet to directly heat the gas separation box. The cold end of the semiconductor refrigerating sheet is connected to an air pump, and the air-distributing box is cooled through the air pump. Install a humidity sensor before the gas inlet of the gas separation box. The control module turns on the semiconductor refrigeration sheet when the humidity of the gas measured is greater than the set value upper limit (the upper limit of the set value can be 60%, 65%, 70%, etc.); when the gas humidity measured by the humidity sensor is less than the lower limit of the set value (the lower limit of the set value can be 40%, 50%, etc.), the control module makes the semiconductor refrigeration sheet stop heating and dehumidifying.

Compensation of Flow Rate, Temperature, Power and Pipeline Length

Figure 9:
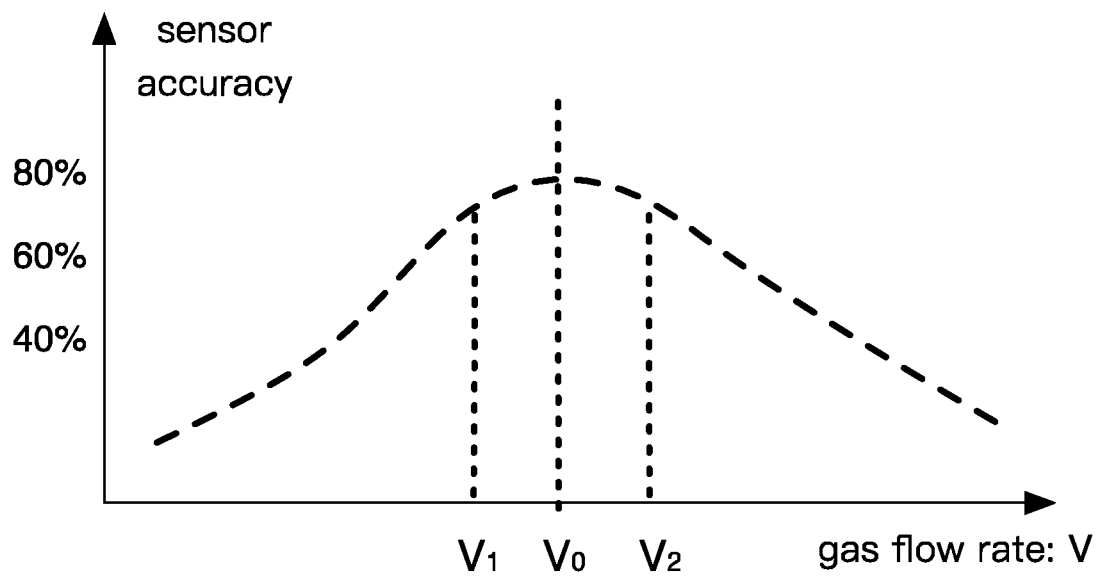
FIG. 9 shows the relationship between the detection accuracy of the sub-sensor and the measured gas flow rate.
Figure 10:
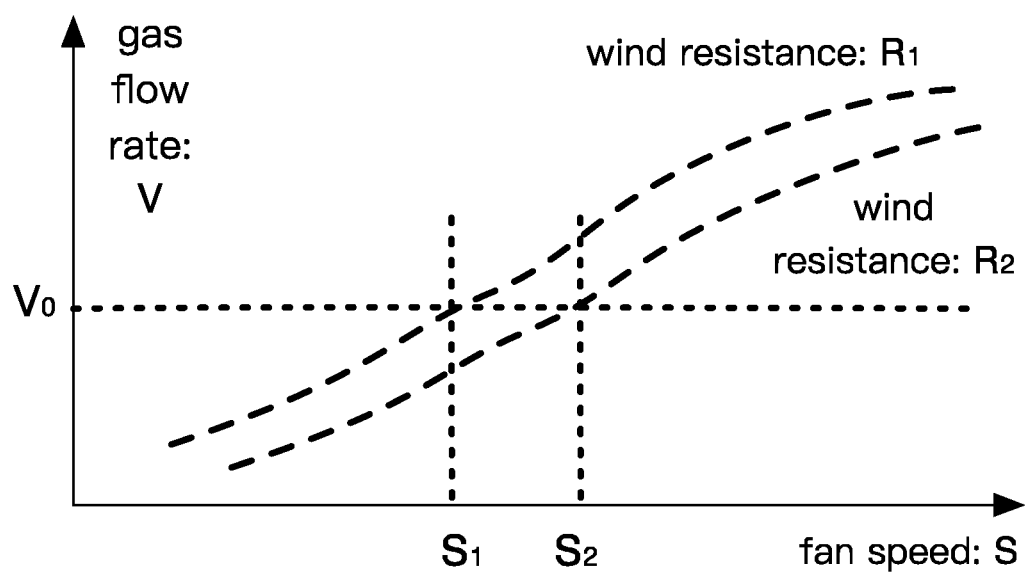
FIG. 10 is a schematic diagram showing the relationship between fan speed, wind resistance and measured gas flow rate.

The detection accuracy of the sub-sensor is also related to the flow rate of the measured gas flowing inside the sensor. As shown in FIG. 9, the detection accuracy of the measured gas is within the range of $V_1$ to $V_2$ with the optimal flow rate $V_0$ as the center. The detection accuracy will be affected if the measured gas flow rate is too fast or too slow. The internal air resistance of the sensor or other reasons will cause the measured gas flow rate to change. As shown in FIG. 10, the present disclosure controls the measured gas flow rate to the optimal flow rate by adjusting the internal fan speed ($S_1$, $S_2$) or other flow rate adjustment methods.

Within range, improve the detection accuracy of the sub-sensor. Multi-core sensor modules use embedded algorithms to compensate for the problem of asynchronous sampling of multiple sub-sensors caused by different lengths of intake pipes, thereby obtaining more accurate detection data. Similarly, temperature and humidity are compensated by corresponding algorithms to improve data accuracy.

Embodiment Four

By controlling the speed of the fan, the sampling flow is compensated. The flow rate and differential pressure sensor are used to obtain the gas flow rate, and a fan speed control circuit is added at the same time. The fan speed is controlled by the obtained gas flow rate information, so that the sampling gas flow rate is stabilized, within a range of preferred flow rate, as shown in $V_0$ of FIGS. 9 and 10. The optimal flow rate of the sensor is based on experimental methods to obtain empirical values.

Embodiment Five

For the laser particle sensor, multi-core sensors comprise a laser power detection device and a laser power control circuit which are configured to compensate the laser power. The change relationship of the particle concentration value corresponding to each laser power value is obtained experimentally (that is, other conditions are fixed and only the measured conditions are changed to obtain the measurement results). The attenuation data is compensated by the laser power control circuit according to the detection result of the laser power detection device.

Embodiment Six

Take temperature compensation measures for the sensor. Install a temperature acquisition probe on the sensor or the measured gas. First, by using the experimental method or the sensor temperature characteristic data, the change relationship of the pollutant concentration value corresponding to different sampling temperature values is obtained (that is, other conditions are fixed and only the measured temperature conditions are changed). Compensate the output pollutant results based on the collected temperature data during use.

Embodiment Seven

Take humidity compensation measures for the sensor.
Install humidity acquisition equipment to collect the humidity data of the measured gas.
First, by using the experimental method or the humidity characteristic data of the sensor, the change relationship of pollutant concentration values corresponding to different sampling humidity values is obtained (that is, other conditions are fixed and only the humidity conditions of the measured gas are changed).
Compensate the output pollutant results based on the collected humidity data during use.

Output Data Calculation Method

Multi-core sensor modules use multiple sub-sensors to measure air quality at the same time, and the output value is the result of comprehensive calculation of data from multiple sensors. The data is smoother, more stable, and more accurate.

The eighth embodiment to the twelfth embodiment are data calculation methods of the sensor module. The data of the outlier sensor needs to be excluded during data calculation. For the method of determining the outlier sensor, refer to the thirteenth to the seventeenth embodiments.

In the case of the sensor module and the low-frequency calibration module, when the low-frequency calibration module generates data, its data can be used as more reliable detection data to participate in the calculation of the output data of the sensor module.

Considering that the data of the low-frequency calibration module is more reliable, the data of the low-frequency calibration module can be given a double weight to be added to the calculation.

Embodiment Eight

Mean value method: a method for calculating the output data of a sensor module; after excluding abnormal sub-sensor data, the average value of all normal sub-sensor data is taken as the output result.

Embodiment Nine

Median method: a method for calculating the output data of a sensor module; after excluding abnormal sub-sensor data, the values of all normal sub-sensor are sorted, and the middle value of the sort is used as the final result.

The number is even, and then the average of the two sub-sensors in the middle is taken as the final result.

Embodiment Ten

Correlation coefficient method: a method for calculating the output data of a sensor module; after excluding abnormal sub-sensor data, calculate the normal sub-sensor data as follows to obtain the final result.

The storage unit stores the historical detection data of each sub-sensor, and calculates the values of the judged sub-sensor and other sub-sensors by using the historical data of a period (1 minute, 10 minutes, 20 minutes, . . . 1 hour) as a time unit.

Correlation coefficient, the calculation method of the above correlation coefficient:

A. Obtain the value of the historical time unit of the judged sub-sensor and the average value of other sub-sensors in that period to calculate the correlation coefficient.

B. Obtain the value of the historical time unit of the judged sub-sensor to calculate the correlation coefficient with each of the other sub-sensors. After obtaining the result, calculate the average value of each correlation coefficient as the final correlation coefficient to obtain each normal sub-sensor. After correlating coefficients with other sub-sensors, calculate the percentages of the correlation coefficients of all normal sub-sensors to the sum of the total correlation coefficients. Multiply the detection result of each normal sub-sensor by this percentage and add up to get the final detection result.

Embodiment Eleven

Variance method: a method for calculating the output data of the sensor module; after excluding the abnormal sub-sensor data, the normal sub-sensor data is calculated as follows to obtain the final result.

The memory stores the historical detection data of each sub-sensor, and uses the historical data of a period of time (1 minute, 10 minutes, 20 minutes, . . . 1 hour) as the time unit to calculate the variance Vi (or standard deviation), add the variance of each sub-sensor and calculate the difference between the sum and the variance of each sub-sensor. After obtaining the difference, calculate the percentage of the sum of the difference of each sub-sensor. The detection result of the sub-sensor is multiplied by the percentage and then added up to obtain the final detection result.

Embodiment Twelve

Percentage method: A method for calculating output data of a sensor module. After excluding abnormal sub-sensor data, the normal sub-sensor data is calculated as follows to obtain the final result.

The sensor stores the historical detection data of each sub-sensor, and uses a period of time (10 seconds, 20 seconds, etc.) as the time unit to calculate the average value of the detection value in the nearest time unit, and uses the average value to calculate. The above calculation method:

A. Add up the average value of each sub-sensor in the time unit to calculate the percentage of each sub-sensor in the sum, and multiply the detection result of each normal sub-sensor by the percentage to add the final result.

B. Using the calculation method described above, calculate the percentage of each sub-sensor in multiple time units closest to the current, average the percentage of each sub-sensor in multiple time units, and get the average of each sub-sensor in multiple time units closest to the current, the detection result of each normal sub-sensor is multiplied by the percentage and then added up to obtain the final detection result.

Identify Sub-Sensor Working Status

Figure 11:
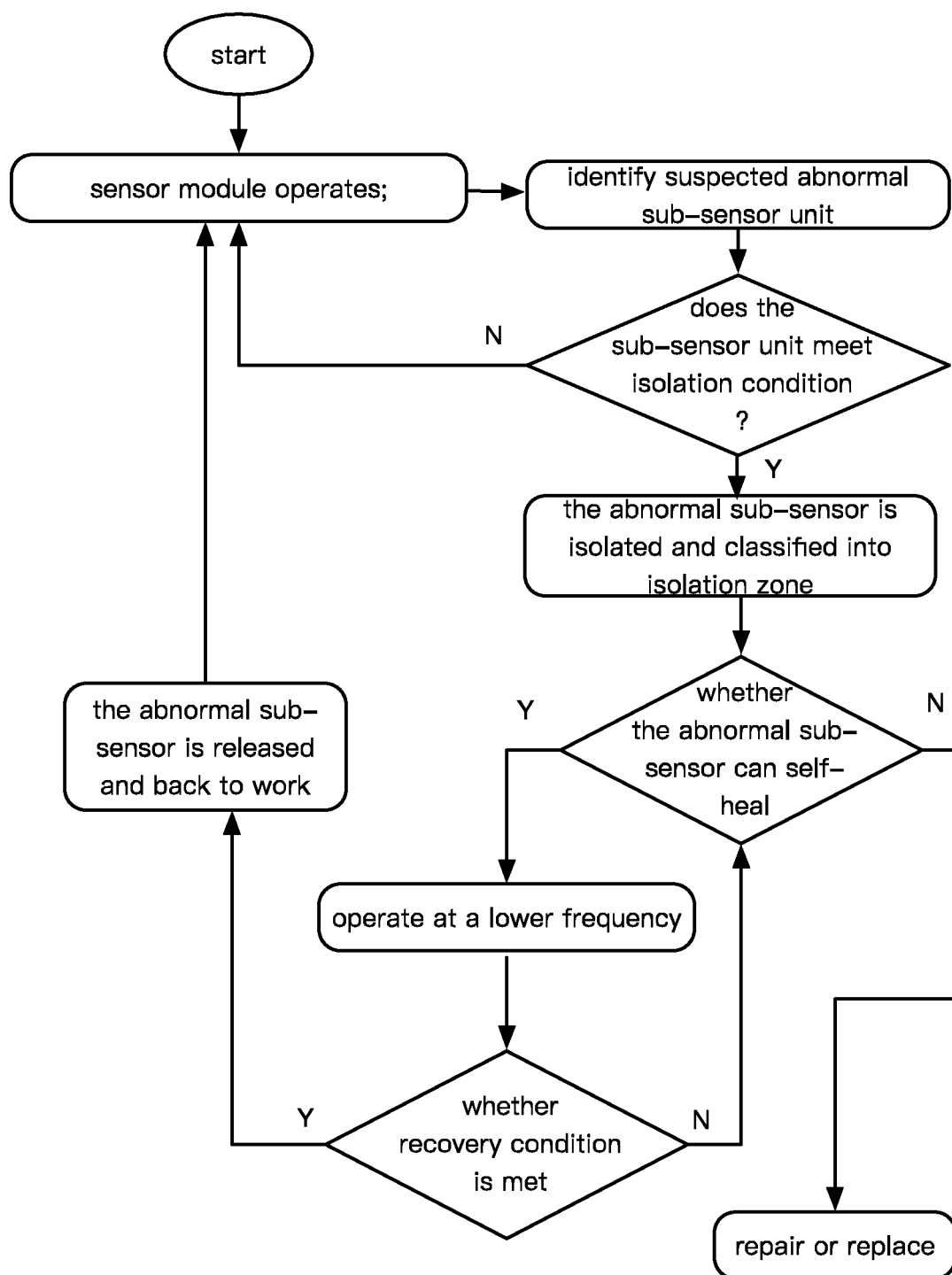
FIG. 11 is a flowchart of a method for isolation and recovery a multi-core sensor system.
Figure 12:
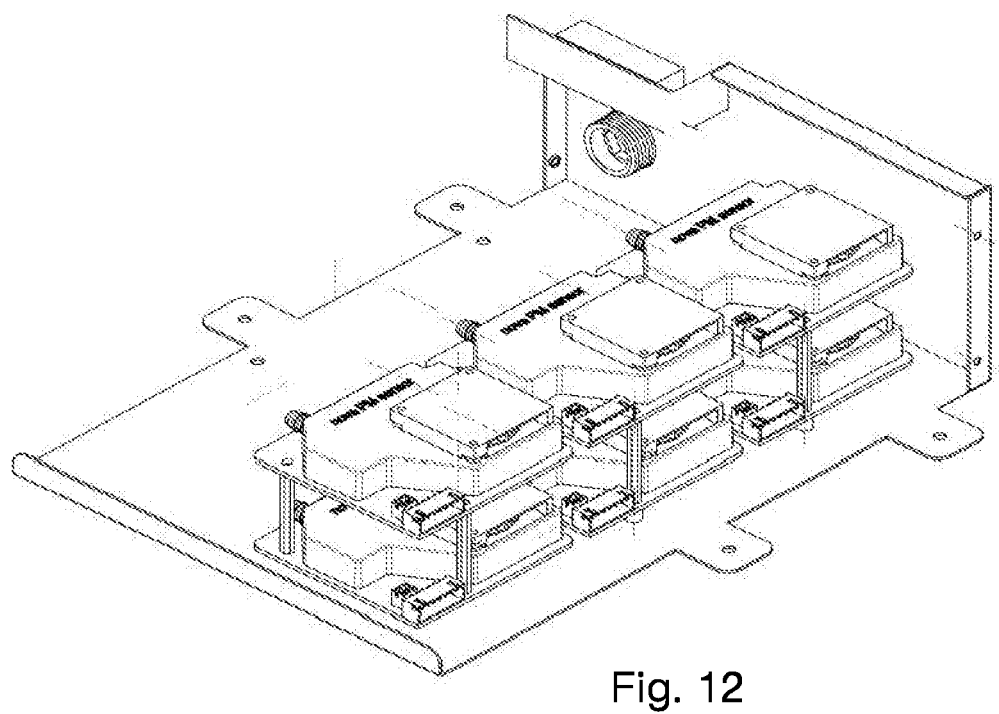
FIG. 12 is a schematic diagram of the six-core sensor module.

This solution provides a method for isolation and restoration for a multi-core sensor system within a taxi. This method is shown in FIG. 11.

1) Judgment of the abnormal sub-sensor: The sensor module obtains a set of detection data at a time, and the control module filters out suspected abnormal data from this set of data, and then determines whether the corresponding sub-sensor meets the isolation condition.

2) Isolation of an abnormal sub-sensor: The sub-sensor was judged to be abnormal sub-sensor and then classified into the isolation zone; the sensor module continues to work after it is degraded. The abnormal sub-sensor entering the isolation zone can stop working or continue sampling and detection, but the data output by the abnormal sub-sensor does not participate in the calculation of the output data of the control module.

3) Determine whether the abnormal sub-sensor entering the isolation zone can heal itself: if it is judged that it can heal itself, then perform frequency reduction work on the self-healing abnormal sub-sensor, and if the abnormal sub-sensor cannot heal itself, the operation and maintenance party is notified for the repair or replacement.

4) Recovery of abnormal sub-sensors: Monitor the output data of the abnormal sub-sensors entering the isolation zone to determine whether they have reached the recovery conditions. If the recovery conditions are met, the sub-sensors meeting the recovery conditions are detached from the isolation zone, and the abnormal sub-sensor is determined as the initial sub-sensor and resume to work.

Embodiment Thirteen

Judgment of suspected abnormal sub-sensor and abnormal sub-sensor: When the variance of the data of a certain sub-sensor exceeds the threshold, or the drift of the data of the sub-sensor exceeds the threshold, first list it as a suspected abnormal sensor instead of immediately identifying the sensor as abnormal. Finally, it is determined that the sub-sensor is abnormal only when multiple consecutive data are abnormal in a certain period of time.

Embodiment Fourteen

Comparison method of average values of sub-sensors: Take a quad-core sensor module as an example, and use the current time as a reference to compare the data of one sub-sensor with the average value of other three sub-sensors within a certain period of time (such as 5 s average, 30 s average, 60 s average, etc.)

Embodiment Fifteen

When the abnormal sub-sensor occurs, the data collected by it should be isolated and not involved in the calculation of the final output data of the sensor module. However, the abnormal sub-sensor still normally outputs data to the control module to monitor the data of the abnormal sub-sensor. Abnormal sub-sensor includes abnormal drift of sub-sensor, abnormal fluctuation of sub-sensor and abnormal correlation of sub-sensor.

The storage unit stores the historical detection data of each sub-sensor, and calculates respectively the value correlation coefficient of the target sub-sensor and other sub-sensors by using the historical data of a period (1 minute, 10 minutes, 20 minutes, . . . 1 hour) as a time unit. If the correlation coefficient is less than a certain value, such as 0.5 (non-strong correlation), the correlation of the sensor is judged to be abnormal, and it does not participate in the calculation of the final result. The specific process of calculating the correlation coefficient is as follows:

A. Obtain the value of the historical time unit of the target sub-sensor and the average value of other sub-sensors in that period to calculate the correlation coefficient.

B. Obtain the value of the historical time unit of the sub-sensor to calculate respectively the correlation coefficient with each of other sub-sensors, and calculate the average value of each correlation coefficient as the final correlation coefficient after obtaining the result.

The correlation method is used to determine the abnormal correlation of sub-sensor. Taking the correlation calculation of a quad-core sensor module as an example, the correlation between the 100 sets of data of the sub-sensors and the average of the 100 sets of data of the other three sub-sensors is used for correlation calculation. If the $R_2$ is less than or equal to 0.8, it indicates that the correlation of the sub-sensors is abnormal, and the sub-sensor data is isolated. The sensor module selects the data of the other three sub-sensors to calculate and output the monitoring results.

Embodiment Sixteen

The sixteenth embodiment is a method for determining the abnormal fluctuation of sub-sensor. The storage unit stores the historical detection data of each sub-sensor, and uses the historical data of a period of time (1 minute, 10 minutes, 20 minutes, . . . 1 hour) as the time unit to calculate the variance (or standard deviation), by comparing the variance (or standard deviation) of the target sub-sensor with the variance (or standard deviation) of other sub-sensors, the specific process of above variance comparison method is as follows:

A. Compare the variance (or standard deviation) of the target sub-sensor with the mean value of the variance (or standard deviation) of other sub-sensors. If the difference between the two exceeds a certain value, such as 20%, 30%, etc., the abnormal fluctuation of the sub-sensor will be judged.

B. Compare the variance (or standard deviation) of the target sub-sensor with the variance (or standard deviation) of other sub-sensors respectively, and calculate the percentage of the difference between the two relative to the variance (or standard deviation) of the compared sub-sensor. Select the maximum value of percentage. If it exceeds a certain value, such as 20%, 30%, etc., it is judged that the abnormal fluctuation sub-sensor.

Embodiment Seventeen

The seventeenth embodiment is a method for judging the abnormal drift of sub-sensor. The difference between the average value of the target sensor in the past two time units is calculated, and the percentage of the difference value and the average value in the latest time unit is calculated, and the percentage is used for judgment. The specific process of above drift judgment method is as follows:

A. Compare the percentage obtained by the target sub-sensor with the average of the percentages obtained by other sub-sensors. If the percentage difference exceeds a certain value, such as 20%, 30%, 40%, etc., the sub-sensor is judged to be drifting abnormally.

B. Compare the percentage obtained by the target sub-sensor with the average of the maximum value obtained by other sub-sensors. If the percentage difference exceeds a certain value, such as 20%, 30%, 40%, etc., the sub-sensor is judged to be drifting abnormally.

Embodiment Eighteen

In the case of the need to isolate the abnormal sensor, the data of the abnormal sensor is isolated, but the fan or air pump of the abnormal sensor continues to keep running, to ensure that the wind pressure and flow are constant, and to reduce pressure fluctuations.

Embodiment Nineteen

Figure 13:
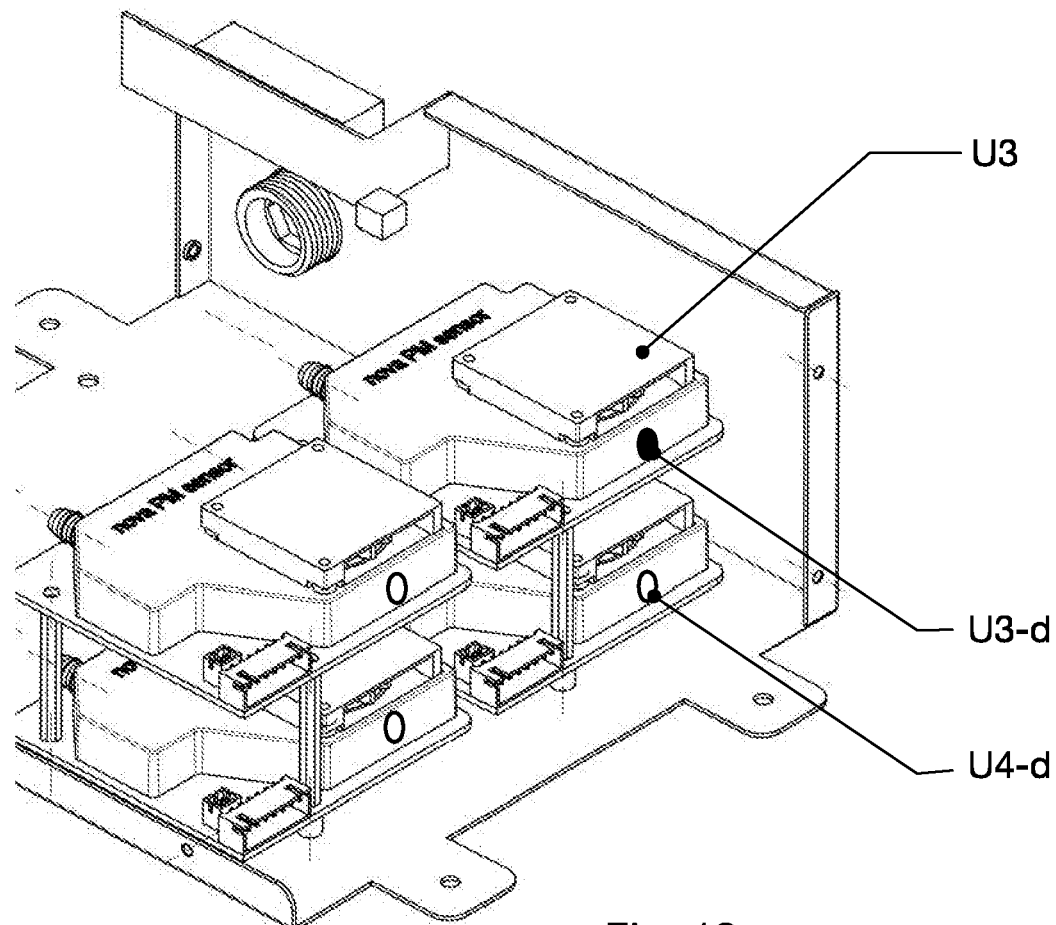
FIG. 13 is a schematic diagram of the quad-core sensor module and its fault indicator.
Figure 14:
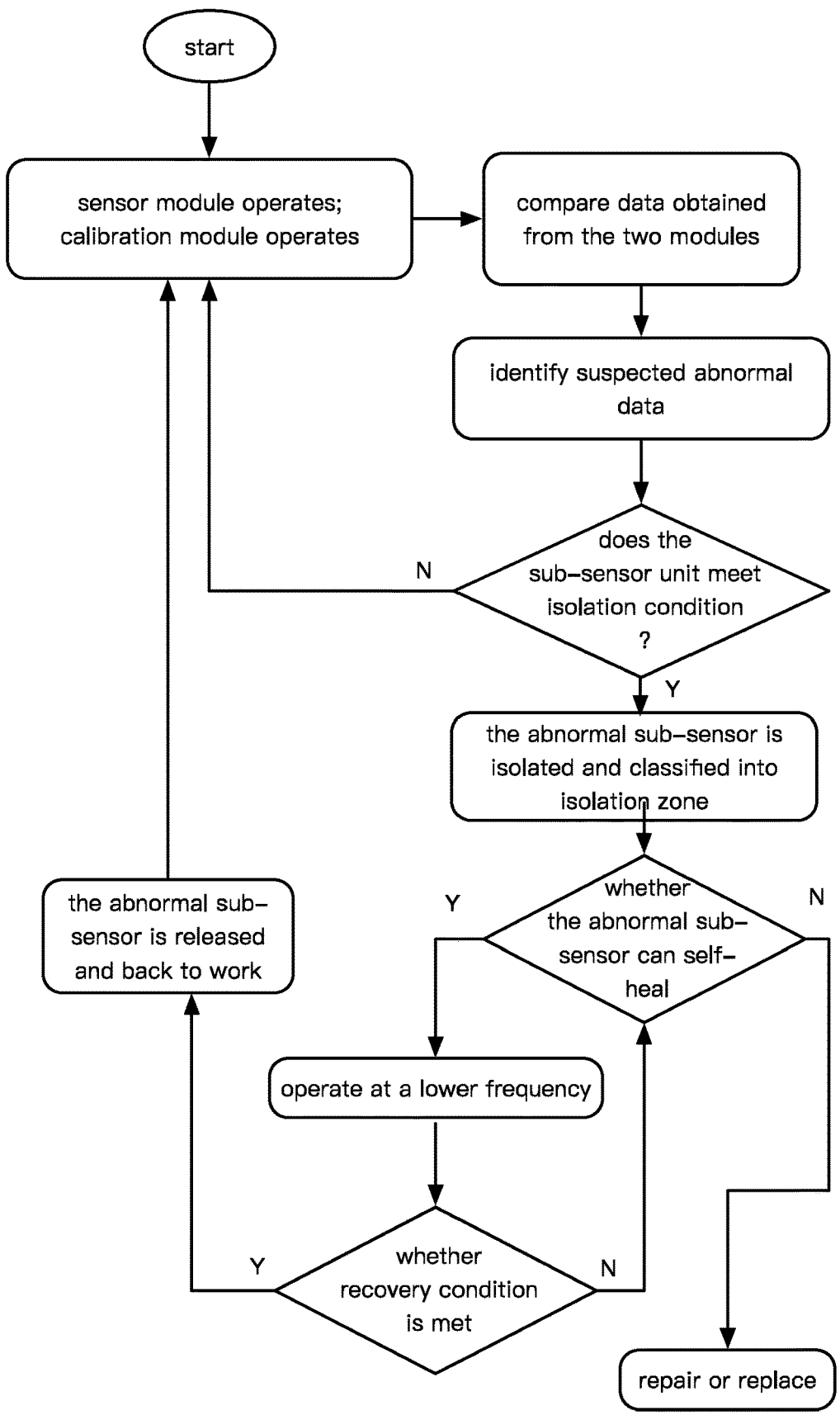
FIG. 14 depicts the process of the isolation and recovery method of a multi-core sensor system.

As shown in FIG. 13, install the status indicator light on the sub-sensor. After the abnormal sub-sensor U3-3 is identified, the status indicator light U3-d at the corresponding position on the communication port of the circuit board will change to a warning color (such as red). The status indicator light U4-d corresponding to the sub-sensor in normal working state is green.

Rotational Rest Mode

The disclosure sets a rotational rest working mode for the sensor module. Among the sub-sensors that work normally, one or more rotation rests are selected, that is, the fatigue problem of the sub-sensor is solved by actively degrading the operation. For the laser sensor module, the rotational rest can also keep the light attenuation of the same group of sensors basically synchronized.

Common single-rotational rest conditions include:
1) The sub-sensor with the longest time to enter the fatigue state;
2) The sub-sensor closest to entering the fatigue state;
3) The sub-sensor with the longest accumulated working time;
4) The sub-sensor with the least accumulated rotational rest;
5) When the temperature data of the sub-sensor can be obtained, the sub-sensor with the highest temperature;
6) Suspected abnormal sensor.

The sub-sensors selected by using different rotational rest conditions may be inconsistent. In actual application, multiple rotational rest conditions may be given weights or priorities to quantitatively determine which sub-sensor is allowed to enter the rotational rest.

Considering that the fatigue problem is a periodic recurrence problem, ideally, each sub-sensor should get a rest cycle before it enters the fatigue state. Assume that the average stable working time of the sub-sensor is T. For the module of N sensors, if the strategy of successive rotational rest of each sub-sensor in the sensor module is adopted, the interval between the two consecutive rotational rests should not be longer than T/N to ensure that each sensor can enter the rotational rest in time.

If T=8 hours, the sensor module consisting of 4 sub-sensors can be rotated every 2 hours using the sequential rotational rest strategy, which can ensure that each sub-sensor can enter the rotational rest before entering the fatigue state.

A status indicator is installed on the sub-sensor. When an abnormal sub-sensor is identified, the color of the status indicator of the light corresponding sub-sensor changes to a warning color; the status indicator light corresponding to the sub-sensor in normal working status is continuous green. The status indicator light corresponding to the sub-sensor that enters the rotational rest state is green that turns on and off alternately.

Embodiment Twenty

The twentieth embodiment is a rotational rest mode of a sub-sensor. For sensor modules, rotational rest refers to turning off the sensing part of one or more sub-sensors within a specified time. For example, the laser particle sensor module using a fan only turns off the laser, and the fan does not turn off.

The off time of the sub-sensor can be a fixed time (such as 1 hour, 2 hours, 3 hours, 4 hours, 5 hours, 6 hours, 7 hours, 8 hours, 9 hours, 10 hours, 11 hours, 12 hours, 24 hours, 2 days, 3 days, 4 days, 5 days, 6 days, or 7 days, etc.), after the closed sub-sensor reaches the closing time, the closed sub-sensor is activated, and then the next sub-sensor that meets the rotational rest condition is closed. The closed time can also be determined according to the working status of other sub-sensors. For example, in a quad-core sensor module with one sub-sensor in the off state. At this time, if the system determines that one of the three sub-sensors in operation has reached the isolation condition and needs to be isolated, the sub-sensor in the closed state should be immediately enabled. The specific rotation conditions can be:

A. Select the rotational rest sensor based on the temperature change. Form 1: Select the sub-sensor with the highest temperature through the acquired sub-sensor temperature data; Form 2: Select the sub-sensor that is turned off according to the ambient temperature. If the ambient temperature is higher than the temperature set value (such as 40 degrees Celsius), it will be numbered turn off sub-sensors in turn;

B. Select the rotational rest sensor by detecting the change in the value. For confirmed suspected abnormal sensor shut down preferentially.

Embodiment Twenty-One

When three-core or more sub-sensors in the quad-core sensor module work normally, a single-core rotational rest scheme can be adopted. The working state of the sub-sensor is greatly affected by temperature. When the temperature is higher than 60° C. or after four hours of normal operation, the adjacent single-core cycle rest is changed, and the rest is rotated in order to reduce the working time of the sub-sensor under high temperature and increase the working time limit of the quad-core sensor.

What is claimed is:

1. A method for isolation and restoration for a multi-core sensor system within a taxi, the taxi comprising a car body, a roof light and a multi-core sensor system; the roof light being installed on the car body, and the multi-core sensor system being installed in the roof light; the multi-core sensor system comprising a control module and a detection module; the detection module comprising a sensor module consisting of at least two sub-sensors of the same type; the detection module further comprising a low-frequency calibration module consisting of at least one sub-sensor that is of the same type as the sub-sensors of the sensor module, wherein the at least one sub-sensor in the low-frequency calibration module operates at a sensing frequency lower than that of the sub-sensors in the sensor module; the method comprising the following steps:

1) judgment of an abnormal sub-sensor: the control module receives a set of detection data obtained by the sensor module, and receives the detection data obtained by the low-frequency calibration module; and the control module filters out suspected abnormal data from the set of detection data obtained by the sensor module together with the detection data obtained by the low-frequency calibration module, by a way of applying a double weight on the detection data obtained by the low-frequency calibration module in filtering out suspected abnormal data, and then determines whether the sub-sensor corresponding to the suspected abnormal data meets an isolation condition;
  2) isolation of the abnormal sub-sensor: a sub-sensor meeting the isolation condition is determined as an abnormal sub-sensor, and is classified into an isolation zone; and the sensor module is degraded and continues to work;
  3) determining whether the sub-sensor entering the isolation zone can heal itself; if it is judged that it can heal itself, then lowering the sensing frequency of the self-healing abnormal sub-sensor, wherein data output by the abnormal sub-sensor does not participate in calculation of the output data of the control module; and notifying an operation and maintenance party for repair or replace for the abnormal sub-sensor which cannot heal itself; and
  4) recovery of the abnormal sub-sensor: monitoring the output data of the abnormal sub-sensor entering the isolation zone to determine whether the abnormal sub-sensor has reached recovery conditions; if the recovery conditions are met, the sub-sensor that meets the recovery conditions is detached from the isolation zone, and the abnormal sub-sensor resumes to work.

2. The method of claim 1, wherein a ratio of sensing frequencies between the sub-sensor of the sensor module and the sub-sensor of the low-frequency calibration module is 2:1, 3:1, 4:1, 5:1, 6:1, 7:1, 8:1, 9:1, 10:1, 15:1, or 20:1.

3. The method of claim 1, wherein the abnormal sub-sensor is judged according to one of the following abnormalities:
  1) abnormal drift of sub-sensor;
  2) abnormal fluctuation of sub-sensor; and
  3) abnormal correlation of sub-sensor.

4. The method of claim 1, wherein a status indicator light is on the sub-sensor; when the abnormal sub-sensor is identified, the status indicator light on the abnormal sub-sensor is changed to a warning color; otherwise, the status indicator light in green.

5. The method of claim 1, wherein the detection module is configured to detect a concentration of atmospheric pollutants; and the control module is configured to receive, analyze and upload the data detected by the detection module.

6. The method of claim 5, wherein after receiving a set of detection data from the detection module, the control module analyses the set of detection data and calculates an output data according to one of the following methods: 1) mean value method; 2) median method; 3) correlation coefficient method; 4) variance method; 5) percentage method, wherein the data of the abnormal sub-sensor is filtered out.

7. The method of claim 5, wherein the accuracy of the multi-core sensor system is improved by one of the following methods:
  1) compensation for lengths difference: embedded algorithms are used to compensate for asynchronous sampling of the sub-sensor caused by different lengths of intake pipes;
  2)
  temperature compensation: a temperature acquisition probe is installed at the sensor or the measured atmospheric gas; by using the experimental method or temperature characteristic data of the sub-sensor, a change relationship of the pollutant concentrations corresponding to different sampling temperatures is obtained; output results of the multi-core sensor system are adjusted according to measured atmospheric gas temperature; and
  3) humidity compensation: a humidity acquisition device is installed to measure gas humidity; by using the experimental method or humidity characteristic data of the sub-sensor, a change relationship of the pollutant concentrations corresponding to different sampling humidity values is obtained; output results of the multi-core sensor system are adjusted according to measured gas humidity.

8. The method of claim 5, wherein the sub-sensor is one of the following sensors: $PM_1$ sensor, $PM_{2.5}$ sensor, $PM_{10}$ sensor, $PM_{100}$ sensor, sulphur dioxide sensor, nitrogen oxide sensor, ozone sensor, carbon monoxide sensor, VOCs sensor, and TVOC sensor.

9. The method of claim 5, wherein the sub-sensor is a laser particle sensor; the multi-core sensor system comprise a laser power detection device and a laser power control circuit; the multi-core sensor system improves the accuracy of detection data of the sensor module by compensation for laser power which comprises the following steps:
  a change relationship of the particle concentration value corresponding to each laser power value is obtained experimentally; and the attenuation data is compensated by the laser power control circuit according to the detection result of the laser power detection device.

* * * * *